(12) United States Patent
Broyles et al.

(10) Patent No.: US 7,718,699 B1
(45) Date of Patent: May 18, 2010

(54) ABSCISSIC ACID AND DERIVATIVES THEREOF FOR THE TREATMENT OF DISEASES

(76) Inventors: Robert H. Broyles, 212 NW. 20th St., Oklahoma City, OK (US) 73103; Robert A. Floyd, 3117 Thorn Ridge Rd., Oklahoma City, OK (US) 73120; Visar Belegu, 218 N. Charles, Apt. 804, Baltimore, MD (US) 21201; Austin C. Roth, 34 River Rd., Apt. 126, Sunderland, MA (US) 01375

( * ) Notice: Subject to any disclaimer, the term of this patent is extended or adjusted under 35 U.S.C. 154(b) by 921 days.

(21) Appl. No.: 11/369,179

(22) Filed: Mar. 6, 2006

Related U.S. Application Data

(60) Provisional application No. 60/658,803, filed on Mar. 4, 2005.

(51) Int. Cl.
*A61K 31/20* (2006.01)

(52) U.S. Cl. .................................................. 514/560
(58) Field of Classification Search ................... 514/560
See application file for complete search history.

(56) References Cited

U.S. PATENT DOCUMENTS

| 3,958,025 | A | * | 5/1976 | Livingston | 514/557 |
|---|---|---|---|---|---|
| 4,434,180 | A | * | 2/1984 | Visscher | 514/557 |
| 5,201,931 | A | * | 4/1993 | Abrams et al. | 504/291 |
| 5,656,474 | A | * | 8/1997 | Tabaeizadeh et al. | 435/209 |
| 2004/0148654 | A1 | * | 7/2004 | Helentjaris | 800/287 |

* cited by examiner

*Primary Examiner*—Raymond J Henley, III
(74) *Attorney, Agent, or Firm*—Dunlap Codding, P.C.

(57) ABSTRACT

The present invention relates generally to the fields of molecular biology and pharmacology. More particularly, it concerns the use of abscissic acid to treat various diseases, including neurodegenerative diseases and neuromuscular diseases.

27 Claims, 3 Drawing Sheets

ABSCISSIC ACID AND DERIVATIVES THEREOF FOR THE TREATMENT OF DISEASES

This application claims the benefit of U.S. Provisional Application Ser. No. 60/658,803 filed Mar. 4, 2005, the entire contents and disclosure of which are specifically incorporated by reference herein without disclaimer.

BACKGROUND OF THE INVENTION

1. Field of the Invention

The present invention relates generally to the fields of molecular biology and pharmacology. More particularly, it concerns the use of abscissic acid to treat various diseases, including neurodegenerative diseases and neuromuscular diseases.

2. Description of Related Art

Although increases in iron have been associated with several diseases, synthetic chemical chelators of iron have side effects that prevent their widespread use in human medicine. Additionally, most synthetic chelators do not penetrate the blood-brain barrier and are thus of very little clinical use (e.g., in treating neurodegenerative diseases such as Parkinson's Disease).

Ferritin H (FH) is a protein which can chelate iron, and FH is produced by organisms including mammals. It has been shown that ferritin-H can also repress the human beta-globin gene (U.S. Application 2002/0128183, incorporated herein by reference in its entirety without disclaimer). Thus, ferritin H could be beneficial in treating diseases which are caused and/or characterized by increases in iron (e.g., Alzheimer's Disease, Parkinson's Disease) and/or diseases which are characterized by the production of a dysfunctional beta-globin (e.g., sickle cell anemia).

There exists a need to selectively induce FH expression with a compound that may be used clinically. Several compounds may be used to induce FH expression; however, problems including lack of selectivity and/or undesirable systemic effects can result from these compounds. For example, free iron itself can induce ferritin synthesis in cells through a regulation that occurs at the translational level of gene expression. However, this induction is not selective since both FH and ferritin-L (ferritin light chain, FL) are produced. Furthermore, the amount of ferritin induced by this mechanism is unlikely to correct the problem of iron overload. Gene therapy administration of ferritin H is described in U.S. application 2002/0128183, which is incorporated by reference herein in its entirety without disclaimer.

Cytokines such as IL-1β, TGFβ, and TNFα may cause a more specific induction of FH at the transcriptional level of gene expression (i.e., selective in the sense that the ferritin-L gene does not respond to these stimuli). However, these cytokines cause significant unwanted systemic effects in humans and experimental animals such as inflammation, thus limiting their clinical potential.

Retinoic acid, a form of vitamin A, is also a ferritin-H inducer. However, high doses of retinoic acid can result in vitamin toxicity.

SUMMARY OF THE INVENTION

The present invention overcomes limitations in the prior art by providing a method of inducing expression of the human ferritin heavy chain (ferritin-H or FH) gene using abscissic acid (ABA), a phytohormone. Methods are provided for the treatment of a disease, e.g., in which excess free iron is present, by the administration of ABA; in certain embodiments, the free iron may be reduced to normal levels through induction of FH by administration of ABA to a subject.

An aspect of the present invention relates to a method for the treatment of a disease comprising administering a therapeutically relevant amount of abscissic acid to a subject in need thereof, wherein the disease is characterized by: an increase in iron in the subject, elevated levels of beta-globin in the subject, or the production of a dysfunctional beta-globin in the subject. The disease may be a neurological disorder, such as a neurodegenerative disease. The neurodegenerative disease may be Parkinson's Disease, Friedreich's ataxia, Huntington's Disease, Alzheimer's Disease, or amyotrophic lateral sclerosis. The disease may be a cancer, a neuromuscular disorder, atherosclerosis, diabetes, hemochromatosis, or a hemoglobinopathy. The hemoglobinopathy may be sickle cell anemia. The subject may be a mammal, such as a human. The abscissic acid may be administered to the subject intranasally, intradermally, intraarterially, intraperitoneally, intracranially, intraarticularly, intrapleurally, intratracheally, intranasally, intravitreally, intratumorally, intramuscularly, intraperitoneally, intrapericardially, orally, topically, locally, via inhalation, via injection, via infusion, via continuous infusion, via localized perfusion bathing a target cell directly, via a catheter, in a lipid composition, or by any combination of the forgoing. The abscissic acid may be administered in a pharmaceutically acceptable carrier, diluent or vehicle. The method may further comprise the administration of an additional therapeutic compound. The additional therapeutic compound may provide a therapeutic effect for the treatment of a neurological disorder, such as a neurodegenerative disease. The additional therapeutic compound may be vitamin A, a vitamin A derivative, a heteroarotinoid, or a tocopherol. The heteroarotinoid may be ShetA4 or ShetA2. The tocopherol may be gamma-tocopherol or gamma-carboxyethyl hydroxychroman (gamma-CEHC). The abscissic acid may be administered in an amount sufficient to reduce the iron concentration in the brain of the subject (e.g., to reduce the iron concentration in a cell in the brain of the subject, and/or to reduce the iron concentration in the blood of the subject). The subject may be a human. The reduction may provide a therapeutic benefit to the human. The abscissic acid may be administered in an amount sufficient to induce ferritin-H synthesis in the brain of the subject. The subject may be a human. The induction may provide a therapeutic benefit to the human.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
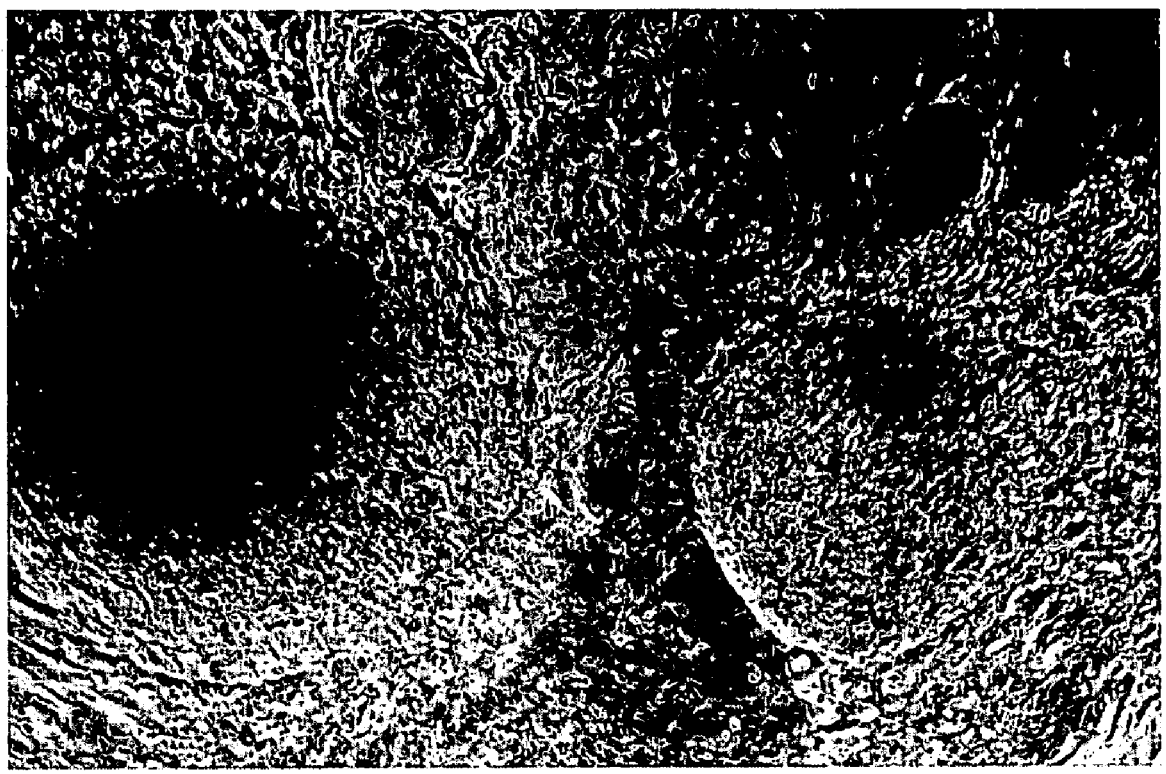
FIG. 1: NT-2 cells cultured as described previously (Paquet-Durand et al., 2003), in the presence of 10 μM RTA for 8 weeks. Organization of large numbers of differentiating neurons into spheres was observed. A phase contrast photo at 100× magnification is shown.

The present invention provides methods of inducing expression of the human ferritin heavy chain (ferritin-H or FH) gene using abscissic acid (ABA), a phytohormone. Methods are provided for the treatment of a disease (e.g., in which excess free iron is present) by the administration of ABA; in certain embodiments, the free iron may be reduced to normal levels through induction of FH by administration of ABA to a subject. In certain embodiments, ABA may be used to induce FH in a cell in vitro or in vivo; in a further embodiment, ABA may be used to induce FH in a cell which is subsequently transplanted into a patient.

I. ABSCISSIC ACID

ABA

Abscissic acid (ABA) is a phytohormone which is structurally similar to retinoic acid (RA). The present invention utilizes ABA, in certain embodiments, to induce ferritin H (FH) expression; in further embodiments, ABA may be comprised in a pharmaceutically acceptable carrier.

Minimal toxicity has been demonstrated due to ABA. ABA has been found in the mammalian brain by two groups (Le Page-Degivry et al., 1986; Pidopliehko and Reymann, 1994), demonstrating that ABA is naturally-occurring in the brain. ABA is a very weak calcium channel blocker (Lynch, 1991; Masters et al., 1994), thus, a therapeutically relevant amount of ABA may be administered to a subject resulting in little or no toxicity due to blockage of calcium channels.

ABA derivatives preferably induce FH. ABA derivatives include, for example, 4' methoxy derivatives of ABA (Asami et al., 2000). Xanthoxine is another ABA derivative.

II. FERRITIN-H (FH)

Two predominant ferritin gene products in humans which are physically and functionally distinct subunits are the ferritin heavy chain (ferritin H or FH) which is 21 kDa, and the ferritin light chain (FL) which is 19 kDa. Mixtures of FH and FL chains make up a 24-mer complex comprising a hollow protein shell capable of storing up to 4,500 $Fe^{3+}$ atoms inside. FH and FL ratios vary from tissue to tissue in the body; embryonic erythroid cells, adult heart, kidney, and brain have significantly higher levels of FH expression than other tissues (Harrison and Arosio, 1996). FH subunits possess ferroxidase activity and promote rapid uptake and oxidation of ferrous ($Fe^{2+}$) iron; in contrast, FL subunits are able to nucleate $Fe^{3+}$ to construct the iron core inside ferritin shells but lack the ferroxidase activity necessary for ferrous iron uptake (Harrison and Arosio, 1996). Recent results show that FL has no direct effect on cellular iron homeostasis by itself, but that the function of FH is to act as an iron buffer (Cozzi et al., 2004).

There exists a significant connection between FH and oxidative stress. Up-regulation or down-regulation of FH or FL have very different effects on cells. Large increases in FL expression resulting from transfection into HeLa cells did not effect the iron availability in these cells but increased the cell proliferation rate in an iron-dependent manner, whereas suppression of FH by siRNA did not increase iron availability but made the cells less resistant to iron supplementation and less resistant to oxidative damage (Cozzi et al., 2004). Mouse brains deficient in H-ferritin have normal iron concentrations but display a protein profile indicating iron deficiency and evidence of increased oxidative stress (Thompson et al., 2003). In mice, a FH knockout displays an embryonic-lethal phenotype (Ferreira et al., 2000). Interestingly, it has been reported that simultaneous over-expression of both FH and FL is implicated in the progression of a newly described neurodegenerative disease in mice that lack iron-regulatory protein-2 that would normally regulate the synthesis of both chains at the translational level (Rouault, 2001).

No toxicity has been reported as a result of over-expression of FH, and beneficial effects have been observed as a result of over-expression of FH. Indeed, the only marked change in ferritin expression that has no reported deleterious effect is over-expression of FH. A number of studies in several cell lines report that great over-expression of FH (e.g., up to several hundred or even 1,000-fold) has beneficial effects which include lowering the labile (free) iron pool, increasing the resistance to oxidative stress, and increasing resistance to apoptosis (Cozzi et al., 2000; Corsi et al., 1998; Picard et al., 1996; Picard et al., 1998; Epsztejn et al., 1999). Thus, previous studies on FH expression in cell lines in culture support the conclusions of Andersen and colleagues that the human FH transgene in mice protects against MPTP-induced PD and mimics the protective effect of the exogenously applied chelator CQ (Kaur et al., 2003).

Strong evidence that FH is a repressor of the human β-globin gene has been observed (Broyles et al., 2001, the entirety of which is herein incorporated by reference without disclaimer). The present invention provides methods for repressing β-globin gene expression (e.g., via induction of expression of FH via administration of ABA).

A. Inducers of FH

A few inducers of the human FH gene are known (Bevilacqua et al., 1994; Bevilacqua et al., 1995; Bevilacqua et al., 1997a; Bevilacqua et al., 1997b; Faniello et al., 2002). These inducers include a B-box-binding transcription factor called Bbf (Bevilacqua et al., 1994; Bevilacqua et al., 1995; Bevilacqua et al., 1997a), and c-Jun/NFY which binds the p300 complex of active chromatin (Faniello et al., 2002). Okadaic acid, a phosphatase inhibitor, stimulates FH transcription in HeLa cells, apparently by increasing the amount of phosphorylated Bbf, thereby increasing Bbf's with the p300 complex on the FH promoter (Bevilacqua et al., 1997b).

Certain cytokines may also be used to induce FH (i.e., IL-1, IL-6, TNF). TNF is less likely to be a satisfactory alternative to ABA since the levels required in vivo to induce FH will likely make a subject (e.g., a mouse or a human) sick and/or result in unacceptable toxic side effects such as inflammation. Cytokines IL-1, IL-6, and TNF have been reported to increase transcription of the FH gene in several mammalian cell types (Harrison and Arosio, 1996).

Retinoic acid (RA) can also induce FH expression. Interestingly, it has been reported that RA regulates FH expression during brain development (VanLandingham and Levenson, 2003). In this study, RA was used to stimulate differentiation of human NTERA-2 embryonal carcinoma (EC) cells into neurons in culture. Differentiation resulted in a 2-fold increase in both FL and FH mRNA, with significant elevations in ferritin expression observed as early as 24 hours after RA treatment (VanLandingham and Levenson, 2003).

ABA has also been reported to induce expression of a plant ferritin that is analogous to human FH, in maize and in Arabidopsis (Fobis-Loisy et al., 1995; Petit et al., 2001). Other plant ferritin genes appear to be more analogous to human FL and, like the human FL gene, are regulated by iron, not ABA. Abscissic acid has been found in mammalian brain (Le Page-Degivry et al., 1986) and has been demonstrated to potentiate NMDA-gated currents in hippocampal neurons (Pidoplichko and Reymann, 1994). Analogues of ABA, but not ABA itself can act as calcium channel blockers in mammalian smooth muscle (Lynch, 1991; Masters et al., 1994). Because ABA has a structure very similar to RA, ABA may also induce FH in stem cells and neuronal precursor cells (e.g., NTERA-2, EC) cells.

III. DISEASE STATES

ABA or an ABA derivative may be used to treat various diseases. In particular, ABA or an ABA derivative may be used to treat diseases which are characterized by increases in iron in a subject (e.g., a human patient) and/or diseases which may be treated (i.e., the symptoms associated with the disease or severity of the disease may be reduced in the subject) by increasing the expression of FH (e.g., where FH chelates iron in a subject and results in a beneficial effect for the subject, or where FH represses β-globin expression). ABA, in certain embodiments, may be used to treat any hemoglobinopathy, spinal disease, and/or neurodegenerative disease. In certain embodiments, ABA may be administered to a subject after traumatic injury (e.g., a brain injury) or to produce a benefit (e.g., reduce inflammation) in a subject with a chronic or an acute disease.

A. Hemoglobinopathies

ABA or an ABA derivative may be used to treat a hemoglobinopathy. Hemoglobinopathy, as used herein, is defined as any disorder caused by or associated with the presence of an abnormal hemoglobin or abnormal hemoglobin levels in the blood of a subject, preferably a human. For example, sickle cell anemia and beta-thalassemias are examples of hemoglobinopathies.

Sickle cell anemia is an example of a hemoglobinopathy that may be treated with ABA or an ABA derivative. Beta-thalassemias (i.e., Cooley's anemia) are another group of hemoglobin diseases. Beta-thalassemias are characterized by a deficiency in the production of beta globin that FH would further inhibit; however, FH may induce gamma-globin (fetal hemoglobin) which, in turn, may substitute for the deficiency in beta globin. It is thus envisioned that ABA or an ABA derivative may also be used for the treatment of beta-thalassemias.

B. Diseases Affecting the Spinal Cord

ABA and derivatives thereof may be used to treat diseases affecting the spinal cord. For example, in certain embodiments, ABA or an ABA derivative may be used to treat amyotrophic lateral sclerosis (ALS). ALS is a disease of the motor tracts of the lateral columns and anterior horns of the spinal cord, which can cause progressive muscular atrophy, increased reflexes, fibrillary twitching, and spastic irritability of muscles. ALS is also referred to as Charcot's disease or Lou Gehrig's disease.

Iron misregulation promotes oxidative stress and abnormally high iron levels have been found in the spinal cords of patients with ALS. Increased free iron in patients with ALS can contribute to the production of nitric oxide, thus promoting oxidative stress; the increased free iron in patients with ALS allows for formation of the dinitrosyl iron complex, which is capable of nitric oxide bio-transformation (Kokic et al., 2005). Reducing free iron in patients in patients with ALS by administering ABA to the patient could thus achieve a therapeutic benefit.

C. Neurodegerative Diseases and Aging

ABA or an ABA derivative may also be used to treat neurodegenerative symptoms associated with neurodegenerative diseases and/or aging. Increases in iron have been observed in aging and neurodegenerative diseases. Age has a powerful effect on enhanced susceptibility to neurodegenerative diseases, especially from oxidative stress which increases in the aging brain (Floyd and Hensley, 2002). The central nervous system is vulnerable to damage from oxidative stress due to several factors that include low levels of glutathione in neurons (Cooper, 1997), membranes that contain a high proportion of polyunsaturated fatty acids (Hazel and Williams, 1990) and a high metabolic activity of the brain that requires high levels of oxygen (Benzi and Moretti, 1995). It is well known that free iron increases in the brain with age and in Parkinson's Disease (PD) (Thompson et al., 2003), and a recent report shows that the rise in free iron in the substantia nigra closely correlates in time with neuron death in a primate PD model (He et al., 2003). The natural iron chelator FH is up-regulated with the age-related increases in iron in certain brain regions, but this up-regulation of FH is not seen in neurodegenerative diseases such as PD (Faucheux et al., 2002). While the mechanism by which free iron exacerbates PD has not been elucidated, a recent report shows that chelation of free iron, either by an exogenously applied chemical chelator or by expression of FH as a transgenic gene product, prevents experimentally induced PD in a mouse model (Kaur et al., 2003). The expression of human-FH, which was placed under the control of the rat tyrosine hydroxylase promoter (pTH), did not cause an overt phenotype.

In elderly people, vascular alterations and degenerative alterations of the central nervous system (CNS) are two of the most common reasons for illness and death. Oxidative stress increases in the aging brain, with logarithmic age-dependent increases in oxidized proteins and oxidized DNA (Floyd and Hensley, 2002). As noted above, the central nervous system is particularly vulnerable to damage from oxidative stress, due in part to low levels of glutathione in neurons (Cooper, 1997), membranes that contain high proportions of polyunsaturated fatty acids (Hazel and Williams, 1990; Pettegrew et al., 2001), and the high metabolic activity of the brain that requires high levels of oxygen (Benzi and Moretti, 1995). It is well known that free iron increases in the brain with age. Iron is the most abundant transition metal in the brain and is considered to be among the most potent potential toxins to CNS cells (Thompson et al., 2003). Histological and quantitative changes in iron and in proteins responsible for iron homeostasis have been reported in most neurodegenerative diseases, especially those prevalent in aging humans (e.g., Parkinson's Disease and Alzheimer's Disease) (Pinero et al., 2000; Thompson et al., 2001). Thus, in certain embodiments of the present invention, ABA or an ABA derivative may be used to treat neurodegenerative diseases such as Parkinson's Disease and Alzheimer's Disease (AD).

1. Parkinson's Disease

The present invention may be used for treatment of Parkinson's Disease (PD), such as early-stage PD, by induction of endogenous FH, and/or with human stem cell-derived neurons genetically engineered to over-express the human FH gene. These approaches have the potential to halt progression of Parkinson's Disease and prevent the debilitating changes associated with advanced stages of this disorder, without exposing patients to the negative effects of systemic iron chelators. Increasing FH in other brain regions may decrease morbidity associated with aging.

PD is the second most prevalent neurodegenerative disorder in humans; yet, the etiology of PD has yet to be delineated (Maguire-Zeiss and Federoff, 2003). Genetic/familial forms account for a very small percentage of the total PD cases. For the vast majority of PD, the sporadic form, the cause is not known. Environmental factors including pesticides, herbicides, and industrial chemicals have been identified as potential risk factors for PD (Maguire-Zeiss and Federoff, 2003). For example, two pesticides that are known neurotoxins work by different mechanisms: chlopyrifos, a widely used organophosphate pesticide, is an acetylcholinesterase (AchE) inhibitor (Caughlan et al., 2004); and rotenone, which is a mitochondrial complex I inhibitor, produces a PD syndrome in rodents (He et al., 2003). It is possible that, even if there are different triggers for Parkinson's Disease, there is a convergent pathobiologic pathway shared by both familial and sporadic forms of PD, leading to cell death (Maguire-Zeiss and Federoff, 2003; Emerit et al., 2004). For example, mitochondrial dysfunction, apoptosis, and reactive oxygen species (ROS) production may form a common pathogenic mechanism in aging and in neurodegenerative diseases such as Alzheimer's Disease (AD), Parkinson's disease (PD), and amyotrophic lateral sclerosis (ALS) (Emerit et al., 2004). Nitric oxide (NO), a reactive nitrogen species (RNS), which can be produced by three isoforms of NO-synthase in brain, also plays a prominent role in these disorders of aging (Emerit et al., 2004; Tieu et al., 2003).

Alterations in free iron concentrations have been associated with PD. PD patients endure a progressive loss of neurons, especially dopaminergic neurons, in the substantia nigra and other subcortical nuclei of the midbrain (He et al., 2003). The cause of nigral cell death is still largely unknown. Hallmarks of PD also include intracytoplasmic Lewy bodies and abnormal neurites, especially in the subcortical nuclei and hippocampus of affected patients. Iron is associated with several of these hallmarks, and evidence links PD with free radicals generated from iron accumulation in the midbrain (Sipe et al., 2002). A recent report shows that the rise in free iron in the substantia nigra closely correlates in time with neuron death in a primate PD model (He et al., 2003). Although the precise mechanism by which iron exacerbates PD has not been characterized, another recent report shows that chelation of free iron, either by an exogenously applied chemical chelator or by expression of FH as a transgenic gene product, prevents MPTP-induced PD in a mouse model (Kaur et al., 2003).

Thus, iron chelation may offer an approach to treating PD and other neurodegenerative diseases in humans. The exogenously applied chemical chelator used by Andersen and coworkers in this mouse model was clioquinol (CQ), a heavy metal chelator that has also been reported to reduce β-amyloid (Aβ) plaques in a transgenic mouse model of AD (Gouras and Beal, 2001; Cherny et al., 2001). However, CQ was withdrawn from the market due to unacceptable side-effects associated with CQ administration; three decades ago after its use, CQ was linked to some 10,000 cases of a subacute myelo-neuropathy (SMON), primarily in Japan (Cole, 2003). CQ iron chelates were initially implicated because they were found in urine of SMON patients and shown to increase lipid peroxidation, but more recent findings have led to the hypothesis that CQ-zinc chelates were the neurotoxin involved in SMON (Cole, 2003) (not CQ-iron chelates). Thus, the usefulness, efficacy, and safety issues of CQ are being reexamined. CQ does not, however, result in depletion of systemic iron levels, whereas deferrioxamine and other currently used iron chelators do deplete systemic iron (Kaur et al., 2003). The natural iron chelator FH, which was expressed as a transgenic gene product, prevented the induction of PD in mice treated with MPTP whereas non-transgenic controls succumbed (Kaur et al., 2003), and none of the undesirable side effects of exogenously applied chemical chelators have been observed for FH.

Several models exist for testing the utility of a compound on PD. An in vitro model of Parkinson's Disease in which rotenone is used to directly treat cells may be used (Sherer et al., 2002). One may perform experiments to determine the effect of FH induction (e.g., by ABA) on PD using another model of PD (Kaur et al., 2003; Betarbet et al., 2000).

IV. PHARMACEUTICAL PREPARATIONS

Pharmaceutical compositions of the present invention comprise an effective amount of abscissic acid (ABA), derivative of ABA, and/or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains ABA (and/or an ABA derivative) or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The ABA or ABA derivative may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The ABA or ABA derivative may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further, in accordance with the present invention, compositions of the present invention suitable for administration may be provided in a pharmaceutically acceptable carrier with or without an inert diluent. The carrier will typically be assimilable and includes liquid, semi-solid (e.g., pastes), and solid carriers. Except insofar as any conventional media, agent, diluent or carrier is detrimental to the recipient or to the therapeutic effectiveness of a composition contained therein, its use in a administrable composition for use in practicing the methods of the present invention is specifically contemplated. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, (e.g., by solution, suspension, emulsification, admixture, encapsulation, absorption and the like). Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, (e.g., denaturation in the stomach). Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include ABA or an ABA derivative, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also contemplated for use with the compositions and methods of the present invention.

One of ordinary skill in the art would be familiar with the range of techniques that can be employed for dispersing a composition in a lipid vehicle. For example, the ABA or ABA derivative may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In certain embodiments of the present invention, the ABA or ABA derivative may be formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings can prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, ABA or ABA derivative may be administered via a parenteral route. As used herein, the term "parenteral" includes routes that bypass the alimentary tract. Specifically, the pharmaceutical compositions disclosed herein may be administered, in certain non-limiting examples, intravenously, intradermally, intramuscularly, intraarterially, intrathecally, subcutaneous, or intraperitoneally U.S. Pat. Nos. 6,753,514, 6,613,308, 5,466,468, 5,543, 158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered and the liquid diluent may be first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition may be combined with a liquid carrier such as, e.g., water or a saline solution, with or without a stabilizing agent.

C. Miscellaneous Pharmaceutical Compositions and Formulations

In other preferred embodiments of the invention, the ABA or ABA derivative may be formulated for administration via various miscellaneous routes, for example, topical (e.g., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of compounds of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. COMBINATION THERAPIES

It is contemplated that ABA and/or an ABA derivative may be used in combination with another therapy to treat a disease. Additional therapies that may be administered to a patient or subject include pharmaceutical agents, drugs, gene therapies, and surgery. These therapies may be currently known or may be subsequently discovered. It is specifically contemplated that all trans-retinoic acid and other forms of vitamin A, heteroarotinoids (e.g., ShetA4, SHetA2), tocopherols (e.g., gamma-tocopherol, gamma-CEHC) and/or surgery may be used in combination with the present invention. Examples of heteroarotinoids may be found in Brown et al. (2004), Liu et al. (2004), Chun et al. (2003), and Mic et al. (2003). In certain embodiments, vitamin C or alpha tocopherol may be used in combination with the present invention. For example, in the case of the treatment of a neurodegenerative disease such as Parkinson's Disease, various therapies including drug therapies, gene therapies, and surgeries have used with some beneficial effect (Walter and Vitek, 2004; Treat Guidel Med Lett., 2004; Chen et al., 2005). Generally, an agent would be provided in a combined amount with an ABA or ABA derivative effective to provide a beneficial effect in a patient or subject (e.g., effective to result in a reduction in, or alleviation in the symptoms associated with, neuron death in the subject due to trauma or a neurodegenerative disease). This process may involve contacting the cell(s) with an agent(s) and the ABA or ABA derivative at the same time or within a period of time wherein separate administration of the ABA or ABA derivative and an agent to a cell, tissue or organism produces a desired therapeutic benefit. This may be achieved by contacting the cell, tissue or organism with a single composition or pharmacological formulation that includes both an ABA or ABA derivative and one or more agents, or by contacting the cell with two or more distinct compositions or formulations, wherein one composition includes an ABA or ABA derivative and the other includes one or more agents.

The terms "contacted" and "exposed," when applied to a cell, tissue or organism, are used herein to describe the process by which a therapeutic construct of ABA and/or another agent, such as for example a drug for the treatment of a disease, are delivered to a target cell, tissue or organism or are placed in direct juxtaposition with the target cell, tissue or organism.

The ABA or ABA derivative may precede, be co-current with and/or follow the other agent(s) by intervals ranging from minutes to weeks. In embodiments where the ABA or ABA derivative, and other agent(s) are applied separately to a cell, tissue or organism, one would generally ensure that a significant period of time did not expire between the time of each delivery, such that the ABA or ABA derivative and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the ABA or ABA derivative. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the ABA or ABA derivative.

Various combination regimens of the ABA or ABA derivative and one or more agents may be employed. Non-limiting examples of such combinations are shown below, wherein a composition ABA or ABA derivative is "A" and an agent is "B":

A/B/A B/A/B B/B/A A/A/B A/B/B B/A/A A/B/B/B B/A/ B/B B/B/B/A B/B/A/B A/A/B/B AB/AB A/B/B/A B/B/ A/A B/A/B/A B/A/A/B A/A/A/B B/A/A/A A/B/A/A A/A/B/A

Administration of the composition of ABA or an ABA derivative to a cell, tissue or organism may follow general protocols for the administration of a therapeutic, taking into account the toxicity, if any. It is expected that the treatment cycles would be repeated as necessary. In particular embodiments, it is contemplated that various additional agents may be applied in any combination with the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

ABA is a More Potent Inducer of FH than RTA

Ferritin H (FH) can suppress globin expression and chelate iron. The inventors have developed methods of fusing cells in vitro for the purpose of creating cross-species developmental erythroid heterokaryons. Fusing nucleated adult erythroid cells of one species with embryonic/larval erythroid cells of another species led to cross induction of developmentally-specific patterns of globin gene expression, providing evidence for developmental stage-specific trans-acting factors (Barker-Harrel et al., 1988; Broyles et al., 1989). In addition to detecting cross-activation of globin genes, cross-repression was also evident in some experiments involving heterokaryons (Broyles et al., 1994). These results led to a search for a repressor of the human adult β-globin gene, the gene mutated in sickle cell disease. The inventors noted that human K562 cells, an erythroleukemia line that expresses embryonic and fetal globins but no adult β-globin, contains a repressor of the β-globin gene. Looking for the identity of the repressor led to the inventors hypothesis that it is ferritin-H (FH), because of two observations: (1) FH is present in embryonic erythroid cells but not adult erythroid cells; and (2) expression clones of FH had been found to up-regulate embryonic and fetal globin promoters. Thus, the inventors hypothesized that FH was also a repressor of adult globin. Using DNA-binding assays in vitro and functional assays in living cells with co-transfection assays and reporter genes, this hypothesis was substantiated by several studies (Broyles et al., 2001).

Significant work supports the notion of a nuclear form of ferritin (Broyles et al., 2001; Broyles et al., 1995). There are now at least five iron-binding proteins found in the nucleus of mammalian cells, including FH, DMT1, heme oxygenase-1, hepcidin, and cytochrome C.

FH expression may thus be critical in health and disease. Increases in free iron have been seen in the aging brain and in the brains of PD and AD patients, and ferritin-H may provide beneficial attributes of as outlined above. Thus, methods for up-regulating FH in living cells may be beneficial in the clinic. Chelation of free iron by FH in a transgenic mouse can protect the mouse from PD induced by the neurotoxin MPTP (1-methyl-4-phenyl-1,2,3,6-tetrahydropyridine).

NTERA-2 embryonal carcinoma (EC) cells which were isolated from the testicular cancer of an adult human male, called NT-2 cells, were used to test the efficacy of ABA on FH induction. These NT-2 cells are very similar to embryonic stem (ES) cells in their properties. When stimulated with 10

µM all-trans-retinoic acid (RTA) over a period of many weeks, these cells differentiate into neurons in large quantity, organizing themselves in spheres (Paquet-Durand et al., 2003), as shown in FIG. 1.

Induction of FH by retinoic acid (RTA), which has been previously shown (VanLandingham and Levenson, 2003), was compared with induction produced by the phytohormone abscissic acid (ABA). The following methods were used.

Undifferentiated NT-2 cells were split and seeded into 6-well plates at a density of $1 \times 10^5$ cells per well with 2 ml medium (DMEM with 10% FBS and antibiotics). The next day, 2 µl of RTA or ABA dissolved in DMSO was pipeted into each well, with control wells receiving 2 µl DMSO only. Each compound was delivered to different wells in one of three concentrations (1 µM, 10 µM, or 100 µM), and all wells had a duplicate. The cultures were allowed to incubate for 7 days undisturbed except for daily observation. At the end of 7 days, the cells were washed with PBS and lysed in a detergent medium, and the lysates were clarified by centrifugation at 14,000×g for 30 min at 4° C. An equal amount of protein (determined by the BCA assay; Pierce) was layered per gel lane, and SDS gel electrophoresis and western blotting was performed for aliquots of all samples; the blots were probed with an FH monospecific polyclonal antiserum (1° antibody) and a goat-anti-rabbit 2° antibody labeled with Alexa-680 (red) fluorescent dye. Probed blots were visualized and photo-digitized with a LI-COR/Odyssey Photoimaging System set for 680 nm excitation wavelength.

Figure 2:
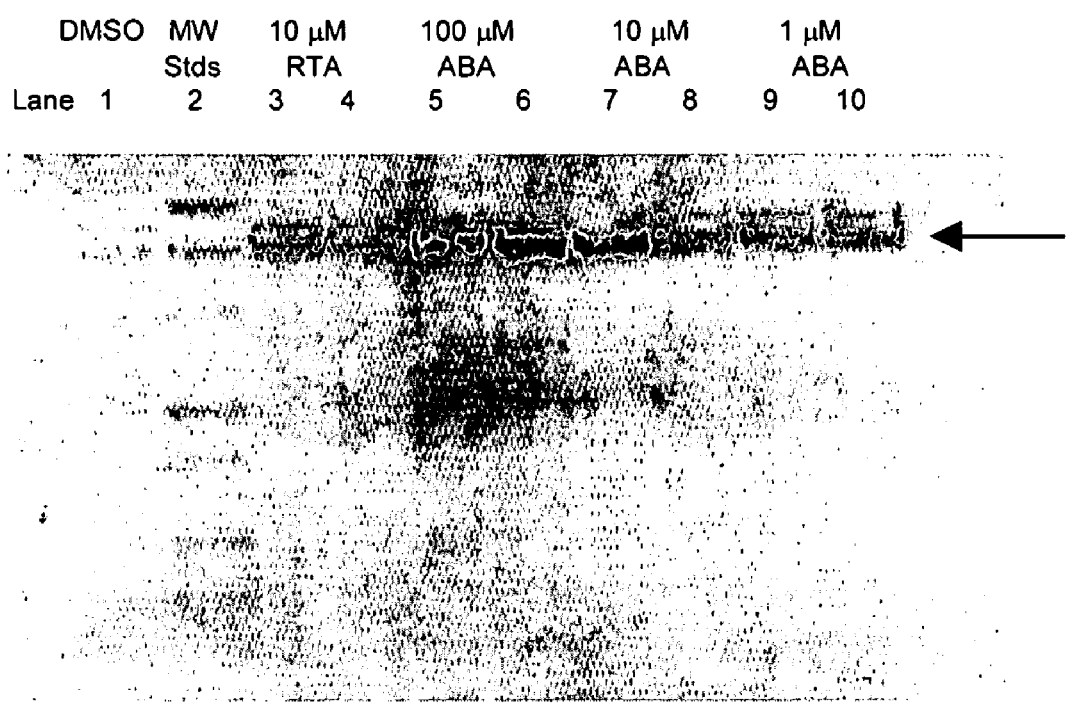
FIG. 2: Western blot results for FH from DMSO-control, RTA-induced, and ABA-induced NT-2 cells cultured in the presence of the inducer for 7 days in each case. The arrow indicates the main FH band. Most of the sample in lane 8 was lost and never entered the gel.
Figure 3:
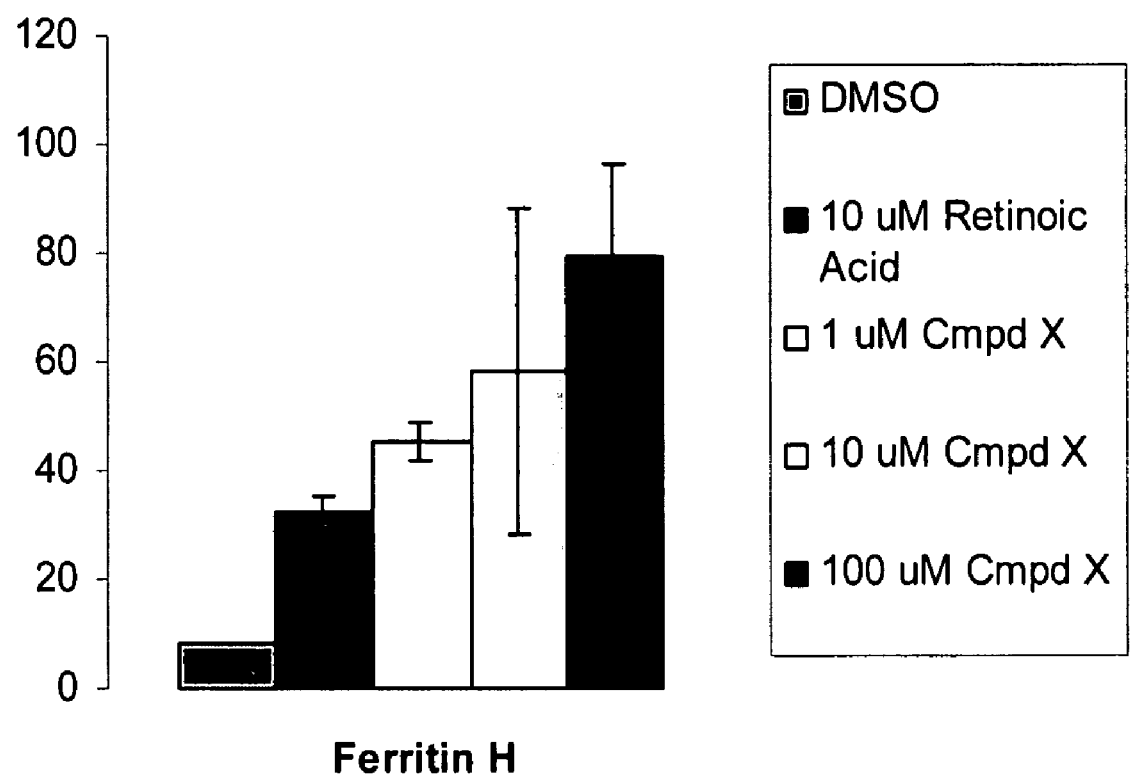
FIG. 3: Quantitation of the western blot results as shown in FIG. 2. The LI-COR apparatus was used to visualize and Odyssey software was used to quantify the stained bands of FH. Bars=Std. Deviations. The bar for 10 μM Cmpd X (ABA, abscissic acid—a compound used for inducing FH in the present invention) is large because of a well-loading/spillover error on this gel.

Results of these experiments are shown in FIG. 2. FH bands (which represent a highly polymerized form of FH) are darker in the samples treated with ABA, as compared to those treated with RTA, and greatly darker than controls. FIG. 3 shows the quantification of these results. This experiment has been replicated two more times with very similar results. Replicate experiments of identical design were also performed with human K562 (erythroleukemia) cells, with comparable results.

CNS cancer cell lines tolerated doses of ABA up to 100 µM for 7 days, supporting the idea of minimal toxicity of ABA. These cell lines included three ATCC lines: a glioblastoma (LN-229), an astrocytoma (U-87 MG), and a neuroblastoma (IMR-32). The latter two cell lines appeared to be have maximum FH production at all times and could not be induced further. The inventors believe this represents the cells' attempt to compensate for the oxidative insult being constantly imposed by the abnormal expression of other genes which characterizes the cancerous state. The LN-229 gliobalstoma line does show some induction of FH by RTA or ABA, as shown for one experiment in Table 1, which gives the relative amount of FH protein expressed per equivalent amounts of total cellular protein per lane on a Western blot. In this case, the amount of induction for RTA and ABA is about the same.

TABLE 1

| Treatment | Relative amount of FH protein |
| --- | --- |
| Vehicle (DMSO) | 71 |
| 10 µM RTA | 114 |
| 10 µM ABA | 105 |

These results support the conclusion that ABA is a much stronger inducer of FH in NT-2 cells than is RTA. Both inducers appear to increase FH an order of magnitude or more over controls, making these very potent inducers of FH in EC cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,363
U.S. Pat. No. 5,466,468
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,613,308
U.S. Pat. No. 6,753,514
U.S. Patent Appln. 20020128183
Asami et al. Bioorg Med Chem Lett., 10:1571-4, 2000.
Barker-Harrel et al., Exp. Cell Res., 178:435-448, 1988.
Benzi and Moretti, Neurobiol. Aging, 16:661-674, 1995.
Betarbet et al., Nat. Neurosci., 3:1301-1306, 2000.
Bevilacqua et al., Biochem. Biophys. Res. Commun., 240: 179-182, 1997.
Bevilacqua et al., Biochem. J., 311(Pt 3):769-773, 1995.
Bevilacqua et al., Gene, 141:287-291, 1994.
Bevilacqua et al., J. Biol. Chem., 272:20736-20741, 1997.
Bhanu et al. Blood. 105(1):387-93, 2005.
Brown et al. J Med Chem. 47(4):1008-17, 2004.
Broyles et al., Dev. Genet., 15:347-355, 1994.
Broyles et al., In: Sickle Cell Disease and Thalassaemias: New Trends in Therapy, Rosa (Ed.), John Libbey Eurotext Limited, France, 43-51, 1995.
Broyles et al., Proc. Natl. Acad. Sci. USA, 98:9145-9150, 2001.
Broyles et al., Prog. Clin. Biol. Res., 83-96, 1989.
Caughlan et al., Toxicol., Sci., 78(1):125-134 2004.
Chen et al., Curr. Gene Ther., 5(1):71-80, 2005.
Cherny et al., Neuro., 30:665-676, 2001.
Chun et al. Cancer Res. 63(13):3826-32, 2003.
Cole, Neuron., 37:889-890, 2003.
Cooper, In: The Molecular and Genetic Basis of Neurological Disease, Rosenberg et al., (Eds.), Butterworth-Heinemann, MA, 1242-1245, 1997.
Corsi et al., Biochem. J., 330:315-320, 1998.
Cozzi et al., Blood, 103(6):2377-2383, 2004.

Cozzi et al., *J. Biol. Chem.*, 275:25122-25129, 2000.
Emerit et al., *Biomed. Pharmacother.*, 58:39-46, 2004.
Epsztejn et al., *Blood*, 94:3593-3603, 1999.
Faniello et al., *Biochem. J.*, 363:53-58, 2002.
Faucheux et al., *J. Neurochem.*, 83:320-330, 2002.
Ferreira et al., *J. Biol. Chem.*, 275:3021-3024, 2000.
Floyd and Hensley, *Neurobiol. Aging*, 23:795-807, 2002.
Fobis-Loisy et al., *Eur. J. Biochem.*, 231:609-619, 1995.
Gouras and Beal, *Neuron.*, 30:641-642, 2001.
Harrison and Arosio, *Biochim. Biophys. Acta*, 1275:161-203, 1996.
Hazel and Williams, *Prog. Lipid Res.*, 29:167-227, 1990.
He et al., *Free Radic. Biol. Med.*, 35:540-547, 2003.
Hwang et al., *Crit. Rev. Ther. Drug Carrier Syst.*, 15(3):243-284, 1998.
Kaur et al., *Neuron.*, 37:899-909, 2003.
Kokic et al. *Redox Rep.* 10(5):265-70, 2005.
Le Page-Degivry et al., *Proc. Natl. Acad. Sci. USA*, 83:1155-1158, 1986.
Liu et al. *J Med Chem.* 47(4):999-1007, 2004.
Lynch, *Gen. Pharmacol.*, 22:895-901, 1991.
Maguire-Zeiss and Federoff, *Ann. NY Acad. Sci.*, 991:152-166, 2003.
Masters et al., *Gen. Pharmacol.*, 25:481-486, 1994.
Mathiowitz et al., *Nature*, 386(6623):410-414, 1997.
Mic et al. *Proc Natl Acad Sci USA.* 100(12):7135-40, 2003.
Paquet-Durand et al., *Brain Res. Dev. Brain Res.*, 142:161-167, 2003.
Petit et al., *Biochem. J.*, 359:575-582, 2001.
Pettegrew et al., *Neurochem. Res.*, 26:771-782, 2001.
Picard et al., *Blood*, 87:2057-2064, 1996.
Picard et al., *J. Biol. Chem.*, 273:15382-15386, 1998.
Pidoplichko and Reymann, *Neuroreport.*, 5:2311-2316, 1994.
Pinero et al., *Cell Mol. Biol.*, 46:761-776, 2000.
Remington's Pharmaceutical Sciences, 18th Ed. Mack Printing Company, 1990.
Rouault, *Nat. Genet.*, 28:299-300, 2001.
Sherer et al., *J. Neurosci.*, 22:7006-7015, 2002.
Sipe et al., *Dev. Neurosci.*, 24:188-196, 2002.
Takenaga et al., *J. Control Release*, 52(1-2):81-87, 1998.
Thompson et al., *Brain Res. Bull.*, 55:155-164, 2001.
Thompson et al., *J. Neurosci. Res.*, 71:46-63, 2003.
Tieu et al., *IUBMB Life*, 55:329-335, 2003.
Treat Guidel, *Med. Lett.*, 2(22):41-46, 2004.
VanLandingham and Levenson, *Nutr. Neurosci.*, 6:39-45, 2003
Walter and Vitek, *Lancet Neurol.*, 3(12):719-728, 2004.

What is claimed is:

1. A method for the treatment of a disease comprising administering a therapeutically relevant amount of abscissic acid to a subject in need thereof, wherein the disease is characterized by:
   1) an increase in iron in the subject,
   2) elevated levels of beta-globin in the subject, or
   3) the production of a dysfunctional beta-globin in the subject.

2. The method of claim 1, wherein the disease is a neurological disorder.

3. The method of claim 2, wherein the neurological disorder is a neurodegenerative disease.

4. The method of claim 3, wherein the neurodegenerative disease is Parkinson's Disease.

5. The method of claim 3, wherein the neurodegenerative disease is Friedreich's ataxia.

6. The method of claim 3, wherein the neurodegenerative disease is Huntington's Disease.

7. The method of claim 3, wherein the neurodegenerative disease is Alzheimer's Disease.

8. The method of claim 3, wherein the neurodegenerative disease is amyotrophic lateral sclerosis.

9. The method of claim 1, wherein the disease is a cancer, a neuromuscular disorder, atherosclerosis, diabetes, hemochromatosis, or a hemoglobinopathy.

10. The method of claim 9, wherein the hemoglobinopathy is sickle cell anemia.

11. The method of claim 1, wherein the disease is a beta-thalassemia.

12. The method of claim 1, wherein the subject is a mammal.

13. The method of claim 12, wherein the mammal is a human.

14. The method of claim 1, wherein said abscissic acid is administered to said subject intranasally, intradermally, intraarterially, intraperitoneally, intracranially, intraarticularly, intrapleurally, intratracheally, intranasally, intravitreally, intratumorally, intramuscularly, intraperitoneally, intrapericardially, orally, topically, locally, via inhalation, via injection, via infusion, via continuous infusion, via localized perfusion bathing a target cell directly, via a catheter, in a lipid composition, or by any combination of the forgoing.

15. The method of claim 1, wherein said abscissic acid is administered in a pharmaceutically acceptable carrier, diluent or vehicle.

16. The method of claim 1, wherein said method further comprises the administration of an additional therapeutic compound.

17. The method of claim 16, wherein said additional therapeutic compound provides a therapeutic effect for the treatment of a neurological disorder.

18. The method of claim 17, wherein said neurological disorder is a neurodegenerative disease.

19. The method of claim 17, wherein the additional therapeutic compound is vitamin A, a vitamin A derivative, vitamin C, a heteroarotinoid, or a tocopherol.

20. The method of claim 19, wherein the heteroarotinoid is ShetA4 or ShetA2.

21. The method of claim 19, wherein the tocopherol is gamma-tocopherol, alpha tocopherol, or gamma-CEHC.

22. The method of claim 1, wherein said abscissic acid is administered in an amount sufficient to reduce the iron concentration in the brain of said subject.

23. The method of claim 22, wherein said subject is a human.

24. The method of claim 23, wherein said reduction provides a therapeutic benefit to said human.

25. The method of claim 1, wherein said abscissic acid is administered in an amount sufficient to induce ferritin-H synthesis in the brain of said subject.

26. The method of claim 25, wherein said subject is a human.

27. The method of claim 26, wherein said induction provides a therapeutic benefit to said human.

* * * * *

UNITED STATES PATENT AND TRADEMARK OFFICE
CERTIFICATE OF CORRECTION

| | | |
|---|---|---|
| PATENT NO. | : 7,718,699 B1 | Page 1 of 1 |
| APPLICATION NO. | : 11/369179 | |
| DATED | : May 18, 2010 | |
| INVENTOR(S) | : Robert H. Broyles et al. | |

It is certified that error appears in the above-identified patent and that said Letters Patent is hereby corrected as shown below:

In the Specification:
Column 15, line 61: After "A/A/B/B" delete "AB/AB" and replace with -- A/B/A/B --.

Signed and Sealed this

Twenty-fourth Day of August, 2010

David J. Kappos
*Director of the United States Patent and Trademark Office*